(12) United States Patent
Slavin et al.

(10) Patent No.: US 7,347,999 B2
(45) Date of Patent: Mar. 25, 2008

(54) METHODS OF TREATMENT OF HEMATOPOIETIC DISORDERS

(75) Inventors: Shimon Slavin, 21 Oren Street, Ein Kerem, 95744 Jerusalem (IL); Olga Gurevitch, Jerusalem (IL); Basan Gowda S. Kurkalli, Jerusalem (IL); Tatyana Prigozhina, Rehovot (IL)

(73) Assignee: Shimon Slavin, Jerusalem (IL)

( * ) Notice: Subject to any disclaimer, the term of this patent is extended or adjusted under 35 U.S.C. 154(b) by 506 days.

(21) Appl. No.: 10/471,048

(22) PCT Filed: Mar. 5, 2002

(86) PCT No.: PCT/IL02/00171

§ 371 (c)(1),
(2), (4) Date: Mar. 31, 2004

(87) PCT Pub. No.: WO02/069988

PCT Pub. Date: Sep. 12, 2002

(65) Prior Publication Data

US 2004/0156834 A1    Aug. 12, 2004

(30) Foreign Application Priority Data

Mar. 5, 2001    (IL) .................................. 141813

(51) Int. Cl.
*A61K 35/32*    (2006.01)
*A61K 35/28*    (2006.01)
(52) U.S. Cl. .............................. 424/93.7; 514/2; 514/8
(58) Field of Classification Search ..................... None
See application file for complete search history.

(56) References Cited

U.S. PATENT DOCUMENTS 5,899,939 A * 5/1999 Boyce et al. ............. 623/16.11

OTHER PUBLICATIONS

Lindholm et al., 1982, Clinical Orthopaedrics and Related Research 171:251-255.*
Connolly et al., 1995, Clinical Orthopaedics and Related Research 313:8-18.*
Armitage, 1994, New England Journal of Medicine 330:827-838.*
An, J. et al., Use of Rat cDNA Probe Specific for the Y Chromosome to Detect Male-Derived Cells, (1997), J. Androl. 18 (3) : pp. 289-293 (Exhibit 1).
Bentley, S.A., Close Range Cell: Cell Interaction Required for Stem Cell Maintenance in Continuous Bone Marrow Culture, (1981), Exp Hematol, 9, pp. 303-312 (Exhibit 2).
Brenner, M.K., et al., Graft versus leukemia effects after marrow transplantation in man, (1991), Baillieres CLin Haematol, 4(3) pp. 727-749 (Exhibit 3).
Brochstein, J.A., Bone Marrow Transplantation for Genetic Disorders, Oncology, (1992), 6(3), pp. 51-58 (Exhibit 4).
Buckley, R.H., et al., haploidentical Bone Marrow Stem Cell Transplantation in Human Severe Combined Immunodeficiency, ((1993) Sein Hematol, 30 (4, Suppl 4) pp. 92-101 (Exhibit 5).
Champlin, R., Immunobiology of Bone Marrow Transplantation as Treatment for hematologic malignancies, (1991), Transplant Proc, 23(4) pp. 2123-2127 (Exhibit 6).
Dorshkind, K., Regulation of hemopoiesis by bone marrow stromal cells and their products, (1990), Ann Rev Immunol, 8, pp. 111-137 (Exhibit 7).
El-Badri, N.S., et al., Osteoblasts promote engraftment of allogeneic hematopoietic stem cells, (1998), Exp Hematol, 26, pp. 110-116 (Exhibit 8).
Enright H., et al., Chronic myelogenous leukemia, (1995), Curr Opin Hematol, 2(4) pp. 293-299 (Exhibit 9).
Gidali, J. et al., Blast Colony Forming Cell-Binding Capacity of Bone Marrow Stroma from Myelodysplastic Patients, (1996), Stem Cells, 14(5), pp. 577-583 (Exhibit 10).
Gurevitch, O.A. et al., The Ability of Induced Osteo-Progate Cells to maintain and Rebuild Long-Term Ectopic Osteo-Hematopoietic Foci In vivo, (1990),Int. J. Cell. Clon 8, pp. 130-137 (Exhibit 11).
Gurevitch, O.A., et al., Ability of Hemopoietic Microevnironment in the Induced Bone to Maintain the Proliferative Potential of Early Hemopoietic Precursors, (1993), Stem Cells, 11, pp. 56-61 (Exhibit 12).

(Continued)

*Primary Examiner*—Elizabeth C. Kemmerer
(74) *Attorney, Agent, or Firm*—John P. White; Cooper & Dunham LLP

(57) ABSTRACT

A composition comprising bone marrow cells (BMC) and demineralized bone matrix (DBM) and/or mineralized bone matrix (MBM), optionally comprising bone morphogenetic protein (BMP), particularly for use in bone marrow transplantation, into bone marrow cavity or into extraskeletal sites, and methods of transplantation/implantation thereof. The composition and methods of the invention enable restoring and/or enhancing the formation of hematopoiectic microenvironment originating from the transplanted BMC, and are useful in the treatment of hematopoietic disorders, such as deficiency of stem cells and/or their products, genetic conditions resulting in abnormal stem cells and/or products, or hematopoietic disorders of malignant or non-malignant origin. The composition and method of the invention may also be used for the induction of graft tolerence, for the prevention of graft-v-host disease. It is mostly important that the compositions and methods of the invention may be applied for the treatment of diseases affecting primarily or secondarily the stromal microenvironment that supports and regulates hematopoiesis. Further provided is a kit for transplantation into a mammal of BMC in admixture with DBM and/or MBM.

8 Claims, 6 Drawing Sheets

OTHER PUBLICATIONS

Gurevitch, O.A., et al., Transplantation of allogeneic or xenogeneic bone marrow within the donor stromal microenvironment, (1999), Transplantation, 68, pp. 1362-1368 (Exhibit 13).

Gurevitch, O.A., et al., , Hematol Tansfusiol, 34, pp. 43-45, (Exhibit 14).

Hisha H., et al., Successful bone marrow transplantation by bone grafts in chimeric-resistant combination, (1995), Exp Hematol, 23, pp. 347-352 (Exhibit 15).

Ishida, T., et al., Requirement of Donor-Derived Stromal Cells in the Bone Marrow for Successful Allogeneic Bone Marrow Transplantation, (1994), J. Immunol, 152, pp. 3119-3127 (Exhibit 16).

Koijima S., Hematopoietic growth factors and marrow stroma in aplastic anemia, (1998), Int J. Hematol, 68(1), pp. 19-28 (Exhibit 17).

Lazarus, H.M., et al., Prevention and treatment of acute graft-versus-host disease: the old and the new. A report from the Eastern cooperative Oncology Group (ECOG), (1997), Bone Marrow Transplant, 68(1), pp. 19-28 (Exhibit 18).

Lazarus, H.M., et al., Ex vivo expansion and subsequent infusion of human bone marrow-derived stromal progenitor cells (mesenchymal progenitor cells): implications for therapeutic use (1995), Bone Marrow Transplantation, 16, pp. 557-564 (Exhibit 19).

Nakagawa T, et al., Prevention of Autoimmune Inflammatory Polyarthritits in Male New Zealand Blank/KN Mice by Transplantation of Bone Marrow Cells plus bone (Stromal Cells), (1993), Arthritis and Rheumatism, 36, pp. 263-268 (Exhibit 20).

O'Flaherty, E., et al., Bone marrow stromal function from patients after bone marrow transplantation, (1995), Bone Marrow transplant, 15, pp. 207-212 (Exhibit 21).

Quinones, R., Hematopoietic Engraftment and Graft Failure After Bone Marrow Transplantation, (1993), American J. Pediatric Hematology/Oncology, 15(1) pp. 3-17 (Exhibit 22).

Reisner, et al., Bone marrow transplantation across HLA barriers by increasing the number of transplanted cells, (1995) Immunol Today, 16, pp. 437-440 (Exhibit 23).

Rowe, J.M., et al., Recommended Guidelines for the Management of Autologous and Allogeneic Bone Marrow Transplantation, (1994), Ann Intern Med., 120(2), pp. 143-158 (Exhibit 24).

Sanhu, J.S., et al., Human hematopoyesis in SCID Mice Implanted with Human Adult Cancellous Bone, (1996), Blood, 88(6) :1973-1982 (Exhibit 25).

Slavin, et al., Control of replase due to minimal residual disease (MRD) by cell-mediated cytokine-activated immunotherapy in conjunction with bone marrow transplantation, (1991), Curr Opin Oncol, 3(2), pp. 254-271 (Exhibit 26).

Slavin, et al., New developments in bone marrow transplantation, (1991), Baillieres Clin Haematol, 4(3), pp. 715-725 (Exhibit 27).

Smith, R., Regulation of Hematopoieses, (1990), Yale J. Biol Med, 63, pp. 371-380 (Exhibit 28).

Sykes, M., et al., Bone marrow transplantaiton as a means of inducing tolerance, (1990), Semin Immunol, 2, pp. 401-417 (Exhibit 29).

* cited by examiner

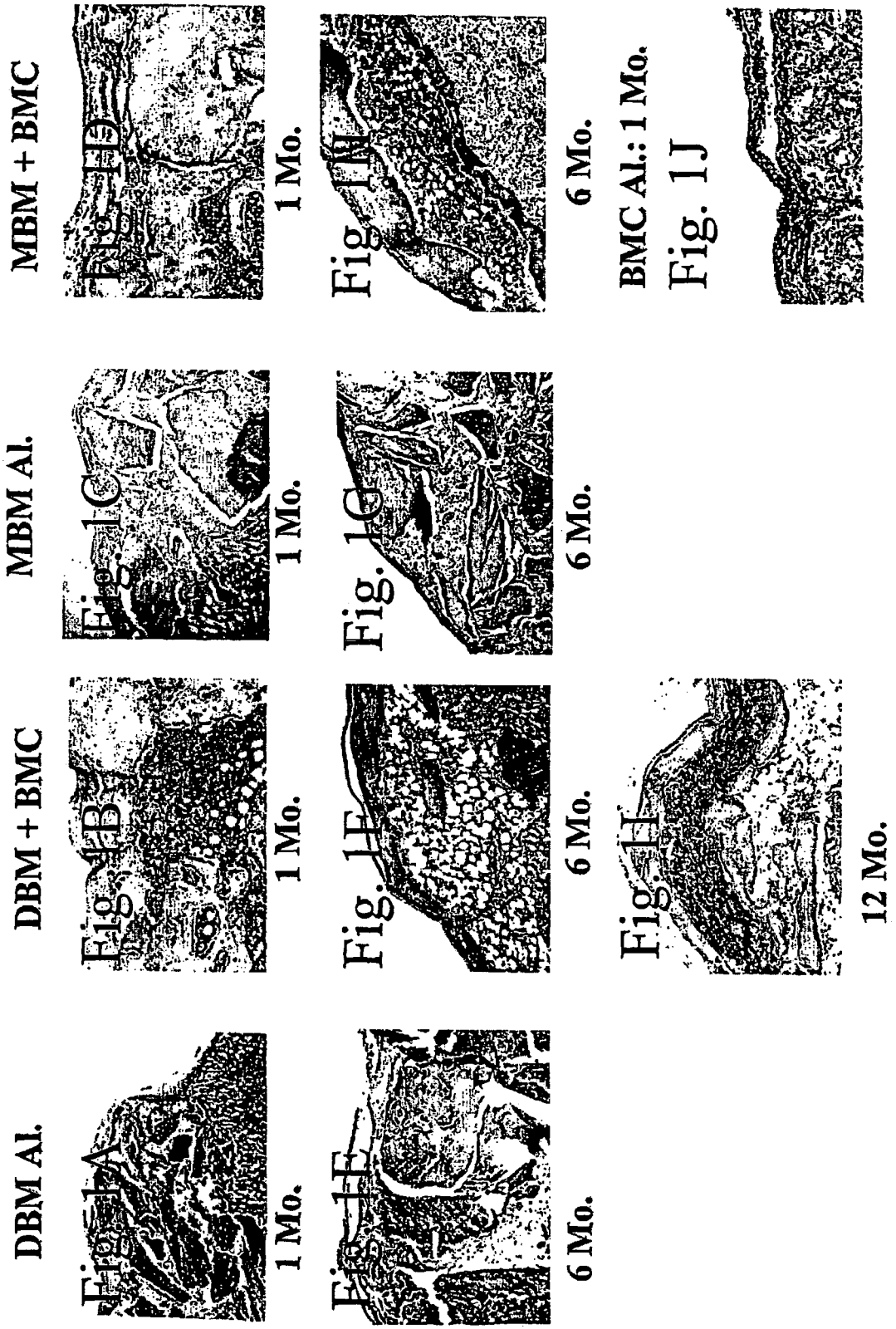

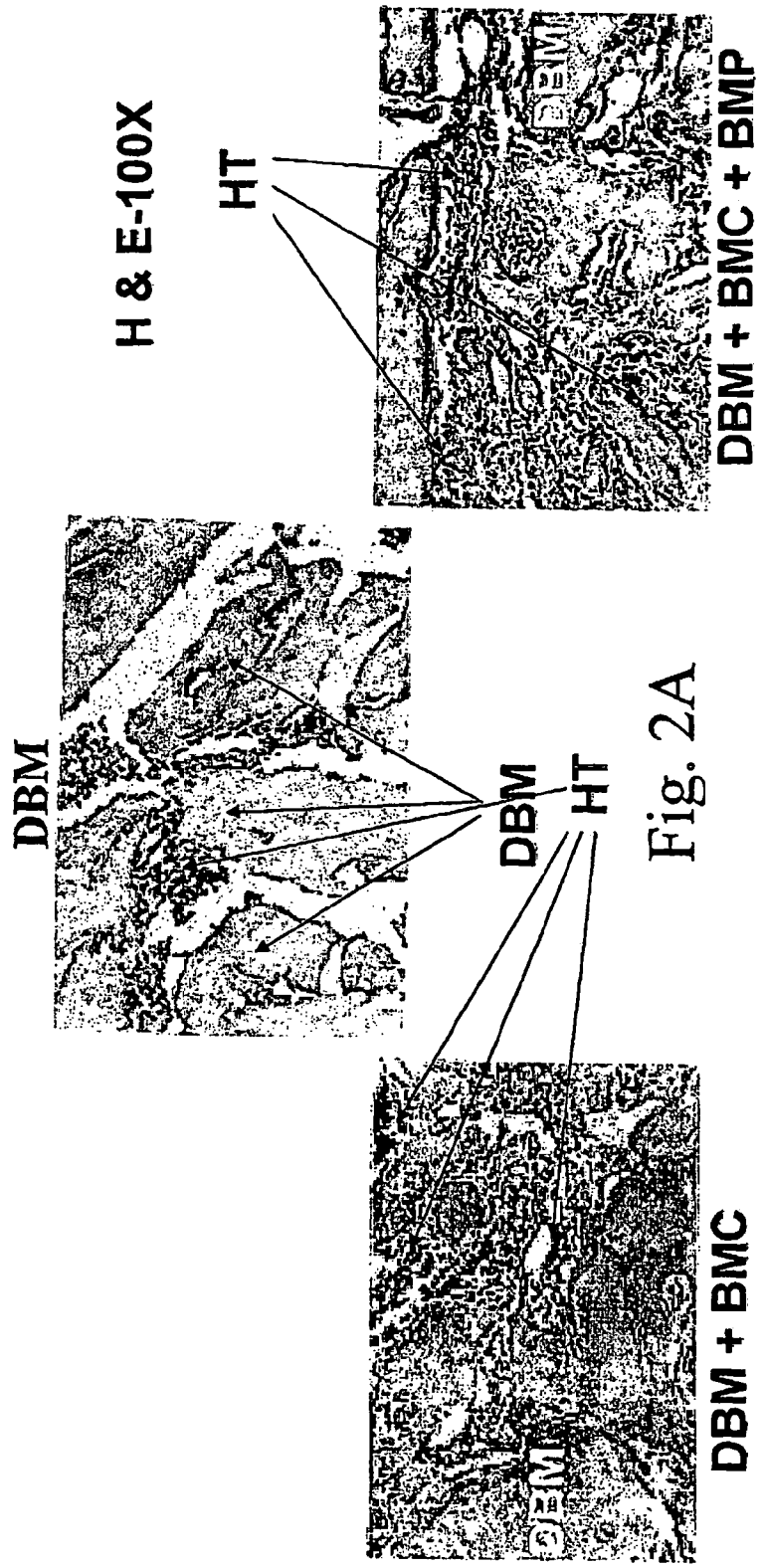

Fig. 3A: D. 0 Po. Abl.
Fig. 3B: D. 30 Po. Transpl.
Fig. 3C: D. 30 Po. Transpl. + *BMP*
Fig. 3D: D. 60 Po. Transpl.
Fig. 3E: D. 150 Po. Transpl.
Fig. 3F: N. Abl.Fe. Bo.

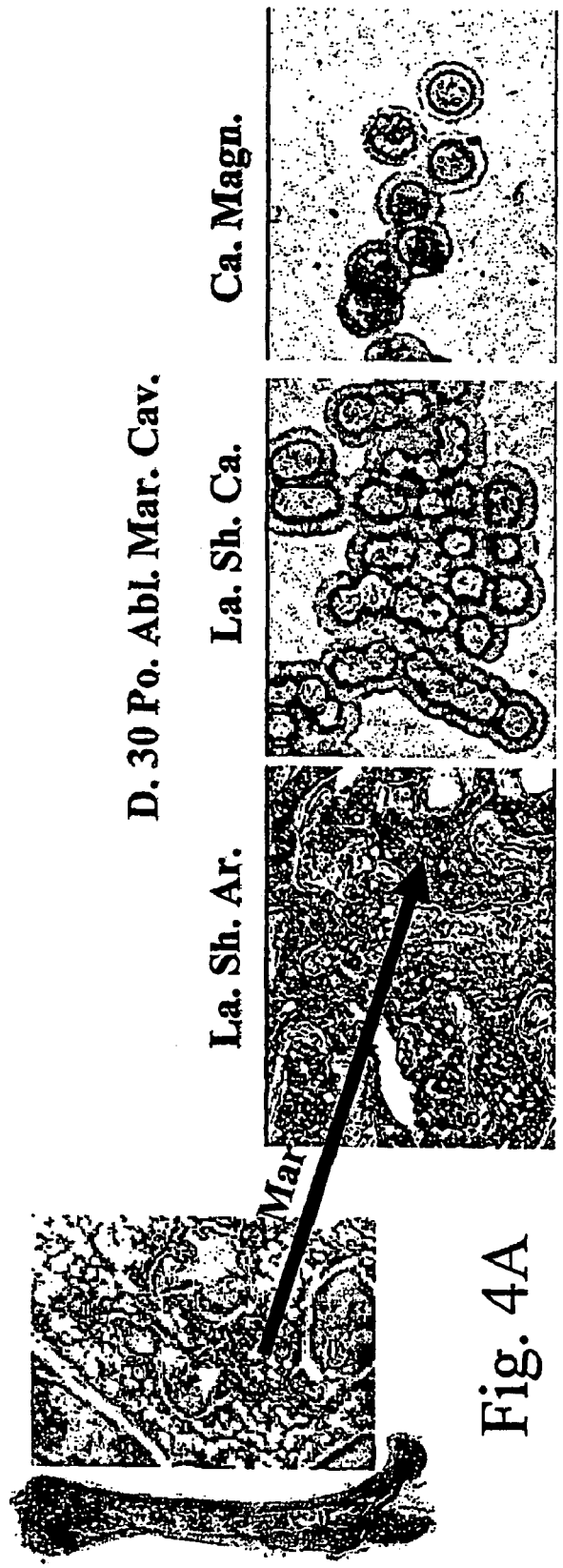

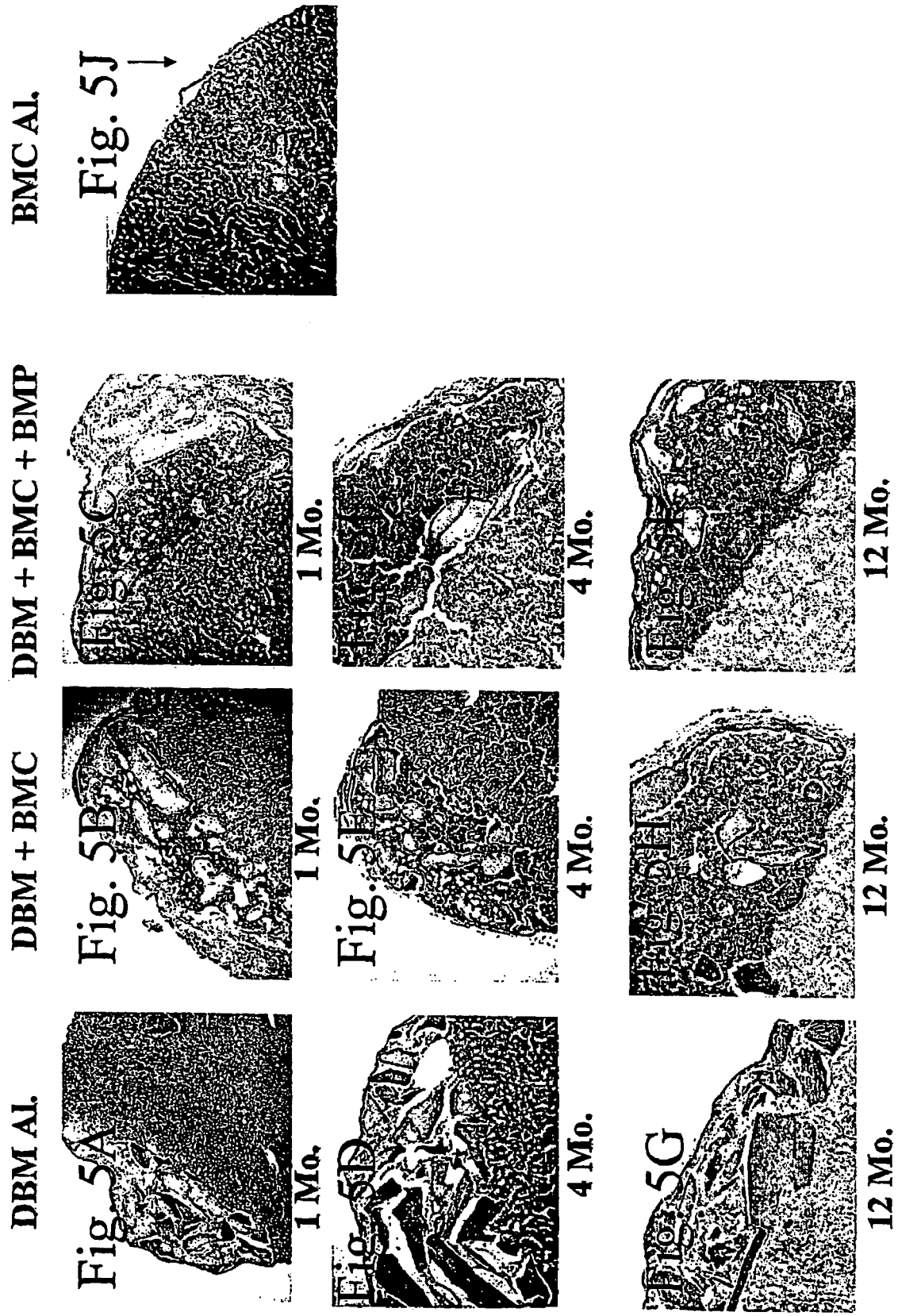

METHODS OF TREATMENT OF HEMATOPOIETIC DISORDERS

This application is a §371 national stage of PCT International Application No. PCT/IL02/00171, filed Mar. 5, 2002, designating the United States of America, which claims priority of Israeli Application No. 141813, filed Mar. 5, 2001, the contents of which are incorporated by reference.

FIELD OF THE INVENTION

The present invention relates to compositions comprising bone marrow cells (BMC) and demineralized and/or mineralized, bone matrix (DBM and MBM, respectively) and to their novel uses in bone marrow transplantation. The compositions of the invention may be particularly effective in restoring the stromal microenvironment, supporting hematopoiesis and developing hematopoietic tissue.

BACKGROUND OF THE INVENTION

It is well known that development and function of the hematopoietic system is supported and regulated by its microenvironment of stromal origin (post-natally, hematopoiesis is totally restricted to skeletal bones) [Dorshkind, K (1990) *Ann Rev Immunol* 8:111; Bentley, S. A. (1981) *Exp Hematol* 9:303; Smith, B. R. (1990) *Yale J. Biol Med* 63:371-380].

Normal bone marrow function depends on co-existence of normal hematopoietic stem cells and its microenvironment, mostly located in the medullary part of the bones. Stem cells cannot function properly in the absence of an adequate microenvironment. Whereas in malignant and non-malignant hematologic diseases caused by deficiency or abnormal stem cells, stem cell transplantation is the treatment of choice that results in cure, in diseases such as myelodysplastic syndrome (MDS), myelofibrosis and other conditions associated with abnormal microenvironment, pancytopenia may occur despite presence of apparently normal hematopoietic cells with no recognizable cytogenetic abnormality. Indeed, in such patients, correction of refractory anemia may sometimes be accomplished following autologous bone marrow transplantation, although the success rate is rather poor in comparison with the outcome of transplants in other hematologic malignancies. In MDS with excess blasts (also known as refractory anemia with excess blasts, RAEB), with blastic transformation (RAEB-T), or with fully overt leukemia, the disease is usually caused by a combination of malignant marrow stem cells and abnormal marrow microenvironment. The success rate in terms of engraftment and disease-free survival in patients with MDS is lower than that observed in patients with acute and chronic leukemia, most likely due to the fact that the replacement of stem cells alone may not be sufficient for a proper engraftment and normal bone marrow function. Theoretically, one could improve the outcome of bone marrow transplantation (BMT) by both replacing abnormal stem cells and providing new microenvironment.

Allogeneic BMT involves the transfer of allogeneic marrow stem cells from a healthy donor to a patient in need. Following BMT, the patient's bones and hematopoietic niches are reconstituted with donor cells, and the entire hematopoietic system including red blood cells, platelets, nucleated cells, the circulating and tissue-bound reticuloendothelial system and the entire immune system, are converted to be of donor origin [Slavin S. and Nagler A. (1991) *Curr Opin Oncol* 3(2):254-71]. BMT is widely applicable for treating and correcting a large number of hematopoietic disorders, including a deficiency in any of the bone marrow products, as well as in a need for replacement of abnormal stem cells and in a large number of genetic disorders [Buckley R. H. et al. (1993) *Semin Hematol* 30(4, Suppl 4):92-101; Brochstein J. A. (1992) *Oncology (Huntingt)* 6(3):51-8; discussion 58, 63-6]. Alternatively, BMT is widely used for cancer therapy and for rescue of patients receiving myeloablative chemoradiotherapy [Slavin S. and Nagler A. (1991) id ibid]. There are many additional potential applications for BMT, such as induction of transplantation tolerance in organ transplantation [Sykes M. and Sacks D. H. (1990) *Semin Immunol* 2:401-417], and as a platform for immunotherapy associated with donor lymphocyte infusions [Champlin R. (1991) *Transplant Proc* 23(4):2123-7; Brenner M. K. and Heslop H. E. (1991) *Baillieres Clin Haematol* 4(3):727-49; Slavin S. et al. (1991) *Baillieres Clin Haematol* 4(3):715-25]. Following myeloablative conditioning, BMT can be used for replacing all host immunohematopoietic system with donor type cells. Alternatively, following non-myeloablative conditioning, the role of BMT could be directed to achieving durable engraftment of donor hematopoiesis side by side with host hematopoiesis for induction of mixed chimerism.

Unfortunately, several limitations restrict the applicability of BMT, such as:

1. Certain hematological diseases for which BMT is indicated may also affect the microenvironment of the marrow and, therefore, stem cell transplantation alone may not be sufficient for complete hematological recovery [Enright H. and McGlave P. B. (1995): *Curr Opin Hematol* 2(4):293-9; Koijima S. (1998) *Int J Hematol* 68(1): 19-28; Gidali J. et al. (1996) *Stem Cells* 14(5):577-583].
2. Efficient consistent engraftment of allogeneic bone marrow cells (BMC), especially purified stem cells or T cell-depleted stem cells, requires transfer of a large number of stem cells which may be difficult to obtain or are even unavailable (e.g. cord blood stem cells, with limited number of cells; child to adult transplant; etc.) [Reisner Y. and Martelli M. F. (1995) *Immunol Today* 16:437; Rowe J. M. et al. (1994) *Ann Intern Med.* 120(2):143-58].
3. Stem cell engraftment in patients with hematopoietic disorders, especially in patients who are treated following mandatory conditioning with irradiation or chemotherapy, is considerably less efficient because of the damaged hematopoietic microenvironment [Enright H. and McGlave P. B. (1995) id ibid.; O'Flaherty E. et al. (1995) *Bone Marrow Transplant* 15:207].
4. Allogeneic BMT as applied to date in patients with hematological disorders is frequently complicated by procedure-related toxicity, poor engraftment and anti-host reaction leading to graft-vs-host disease (GVHD) [Lazarus H. M. et al. (1997) *Bone Marrow tranplant* 19:577; Quinones R. R. (1993) *American J. Pediatric Hematology/Oncology* 15(1):3-17].

In view of the above limitations, one of the main objects of the present invention is the improved engraftmient of BMC in recipients with damaged hematopoietic microenvironment. As the inventors have recently shown, transplantation of BMC within donor hematopoietic microenvironment lowered incidence of GVHD [Gurevitch O. A. et al. (1999) *Transplantation* 68:1362-1368]. Therefore, when allogeneic BMT is associated with procedure-related toxicity due to use of immunosuppressants for treatment of GVHD, complications could be avoided. Furthermore, improvement in transplantation procedure resulted in reduction of the number of BMC required for transplantation.

The present inventors have previously shown that induced bones and hematopoietic microenvironment, developed in mice after ectopic implantation of demineralized bone or tooth matrix, reveal the main properties of skeletal bones [Gurevitch O. A. (1990) *Int. J. Cell. Clon* 8:130-137; Gurevitch O. A. and Fabian I. (1993) *Stem Cells* 11:56-61]. The following observations were made:

a. The hematopoietic microenvironment in induced bones is capable of supporting fully developed three-lineage hematopoiesis.

b. The hematopoietic microenvironment in induced bones is capable of maintaining the proliferative potential of hematopoietic stem cells as could be best documented by colony forming units in the spleen (CFU-S).

c. De novo induced hematopoietic microenvironment is capable of long-term maintenance, remodeling and self-renewal without additional application of any exogenous supplement. Once developed, induced bone becomes a permanent structure in ectopic locations with a functionally active hematopoietic niche.

These observations suggest that induction of hematopoietic microenvironment could be a promising approach for correcting stromal and hematopoietic disorders as well as for enhancing hematopoiesis.

Engraftment of transplanted BMC is improved when hematopoietic cells are transferred together with a bone transplant [Ishida T. et al. (1994) *J Immunol* 152:3119-3127; Hisha H. et al. (1995) *Exp Hematol* 23:347-352; Sandhu J. S. et al. (1996) *Blood* 88(6):1973-1982; Nakagawa T. et al. (1993) *Arthritis and Rheumatism* 36:263-268] or injection of stromal cells of the donor origin [Lazarus, H. M. et al. (1995) *Bone Marrow Transplantation* 16:557-564; El-Badri, N. S. et al. (1998) *Exp Hematol* 26:110-116]. In 1999, the present inventors have shown that GVHD is suppressed if hematopoietic BMC are transferred within their own hematopoietic microenvironment [Gurevitch O. A. (1999) id ibid.]. Allogeneic bone marrow was transplanted not in the usual form of a single cell suspension, where only hematopoietic stem cells are capable of engraftment, but in the form of an undisturbed bone marrow plug evacuated from the femural marrow cavity of donor mouse. The donor bone marrow plug was placed under the kidney capsule of the recipient. In this case, which is an almost not clinically applicable, mesenchymal cell present in the transplant in the form of undisturbed multi-cellular structures produce ectopic (extraskeletal) microenvironment for hematopoietic cells transplanted within the same bone marrow plug.

However, transplantation of bone osteoblasts or bone marrow plugs has not yet been widely accepted in clinical practice because of many technical limitations.

A major shortcoming for all current BMC transplantation procedures is their inability to simultaneously transfer both hematopoietic cells and stromal microenvironment supporting hematopoiesis. In BMC transplantation procedures currently used in hematological practice, in fact only hematopoietic cells from donor are engrafted in the recipient.

Based on the notion that BMC may provide a source for both hematopoietic cells and mesenchymal stem cells capable of induced osteogenesis, the inventors propose transplantation of a composition comprising BMC and DBM and/or MBM (materials stimulating and supporting osteogenic development of mesenchymal precursor cells), allowing for simultaneous development of hematopoietic and stromal tissues originating from donor BMC transplant.

More specifically, the composition of the present invention (comprising BMC and DBM and/or MBM) is transplanted directly into a bone marrow cavity of the recipient or extraskeletally, resulting in de novo formation of stromal microenvironment, which will support hematopoiesis, and hematopoietic tissue from the same transplanted BMC suspension.

Therefore, it is a major object of the present invention a mixture of bone marrow cells with demineralized or mineralized bone matrix, for use for transplantation into patients in need of such treatment, as for example patients suffering from a hematological disorder.

These and other objects of the present invention will become apparent as the description proceeds.

SUMMARY OF THE INVENTION

The present invention relates to compositions comprising a mixture of bone marrow cells (BMC) and demineralized and/or mineralized bone matrix (DBM and MBM, respectively) and to their novel uses in bone marrow transplantation.

Thus, in a first aspect, the present invention relates to a composition comprising BMC and DBM and/or MBM.

In a second aspect, said composition comprising BMC and DBM and/or MBM is for use for bone marrow transplantation (BMT) into a mammal, wherein said mammal may be a human. Preferably, the composition of the invention comprises BMC and DBM for use for BMT into a mammal, preferably a human.

The transplantation site of the composition of the invention may be a bone marrow cavity. Alternatively, said transplantation site may be an extra-skeletal site, wherein said extra-skeletal site is selected from the group consisting of the space under the patient's kidney capsule, muscles, abdominal wall, as well as kidney, liver or heart capsule of the allograft for tolerance induction.

In another embodiment, the composition of the invention further comprises a bone morphogenetic protein (BMP).

In yet another embodiment, the DBM and/or MBM comprised within the composition of the invention is of vertebrate origin, and it may be of human origin.

In a further embodiment, the DBM and/or MBM from the composition of the invention are in powder or slice form. The DBM used in the composition of the invention may be of particle size of about 50 to 2500μ. Preferably, the particle size of the DBM is about 250 to 500μ.

The ratio between BMC and DBM comprised in the composition of the invention is 10 parts of BMC concentrate to 0.5 part of DBM (volume/volume), preferably 4 parts of BMC concentrate to 1 part of DBM (volume/volume).

In a yet further embodiment, the composition of the invention is for transplantation into a bone marrow cavity, for restoring and/or enhancing the formation of hematopoietic microenvironment originating from the transplanted BMC. In addition, the composition of the invention is for transplantation into an extra-skeletal site for the development of hematopoietic microenvironment originating from the transplanted BMC. Newly formed hematopoietic microenvironment results from the differentiation of mesenchymal progenitor cells present in the transplanted BMC suspension.

Thus, in a further embodiment, the composition of the invention is for use in the treatment of a patient suffering from a hematopoietic disorder, wherein said hematopoietic disorder is selected from a deficiency of stem cells and/or their products, a genetic or acquired condition which results in abnormal stem cells and/or products and a hematopoietic disorder of malignant origin, as well as diseases affecting primarily either bone structure and/or composition, or stromal microenvironment that supports and regulates hematopoiesis, osteogenesis imperfecta, mucopolysaccharidosis and mucolipidosis.

In another aspect, the invention relates to a method for transplantation/implantation into a mammal of BMC in admixture with DBM and/or MBM, wherein said method comprises introducing into said mammal a mixture of BMC with DBM and/or MBM, said mixture optionally further comprising pharmaceutically acceptable carrier and/or diluent.

In one embodiment, the mixture of the invention is optionally encapsulated within normal tissue membrane and/or within a selective biocompatible membrane that allows penetration of nutrients, cytokines and cells and retains the DBM and/or MBM particles within said membrane(s).

In another embodiment, said mixture is introduced into a bone marrow cavity of said mammal and/or into an extra-skeletal site of said mammal. The extra-skeletal site of transplantation is selected from the group consisting of the kidney capsule, muscles, liver, abdominal wall and blood vessels.

In yet another embodiment, the mixture used in the transplantation method of the invention further comprises a BMP.

In a further aspect, the invention relates to a method of treating a hematopoietic disorder and/or a disorder associated with malformation, malignancy and/or dysfunction of the bone marrow and wherein bone marrow transplantation is required, for a mammal in need of such treatment. Said method of the invention comprises administering into a bone marrow cavity or extra-skeletal site of said mammal a mixture of BMC with DBM and/or MBM, wherein said mixture optionally further comprises a pharmaceutically acceptable carrier and/or diluent.

In one embodiment, said mixture used in said method of the invention optionally further comprises a BMP.

In another embodiment, said method of the invention further comprises administering to said patient a stem cell suspension, preferably by combined intravenous and intraosseous infusion, with or without BMP and/or other factors enhancing the microenvironment development, as for example hematopoietic growth factors.

In yet another embodiment, the BMC used in said method of the invention are allogeneic or said mammal's own.

In yet a further embodiment, the DBM or MBM used in said method of the invention comprises a demineralized and/or mineralized bone slice, respectively.

A last aspect of the invention relates to a kit for transplantation into a mammal of BMC in admixture with DBM and/or MBM, wherein said kit comprises:
 (a) DBM and/or MBM in a compacted form;
 (b) a BM aspiration needle;.
 (c) an intra-osseous bone drilling burr;
 (d) a needle with a thick lumen for infusion of the viscous bone marrow-DBM mixture;
 (e) a 2-way lumen connector for simultaneous mixing of BMC and DBM;
 (f) diluent for dilution of the mixture;
 (g) a medium for maintaining BMC; and optionally
 (h) cryogenic means for handling and maintaining BMC or BMC together with DBM.

BRIEF DESCRIPTION OF THE FIGURES

FIGS. 1A-J: Photomicrographs of rat kidney sections after transplantation under the kidney capsule.

FIG. 1A: 1 month post-transplantation with DBM alone (Picroindigocarmin, PIC, staining).
FIG. 1B: 1 month post-transplantation with BMC+DBM (Hematoxylin-Eosin, H&E).
FIG. 1C: 1 month post-transplantation with MBM alone (PIC staining).
FIG. 1D: 1 month post-transplantation with BMC+MDM (H&E).
FIG. 1E: 6 months post-transplantation with DBM alone (PIC staining).
FIG. 1F: 6 months post-transplantation with BMC+DBM (PIC staining).
FIG. 1G: 6 months post-transplantation with MBM alone (PIC staining).
FIG. 1H: 1 month post-transplantation with BMC+MDM (PIC staining).
FIG. 1I: 1 year post-transplantation with BMC+DBM (PIC staining).
FIG. 1J: 1 month post-transplantation with BMC only (PIC staining).

Figure 4E:
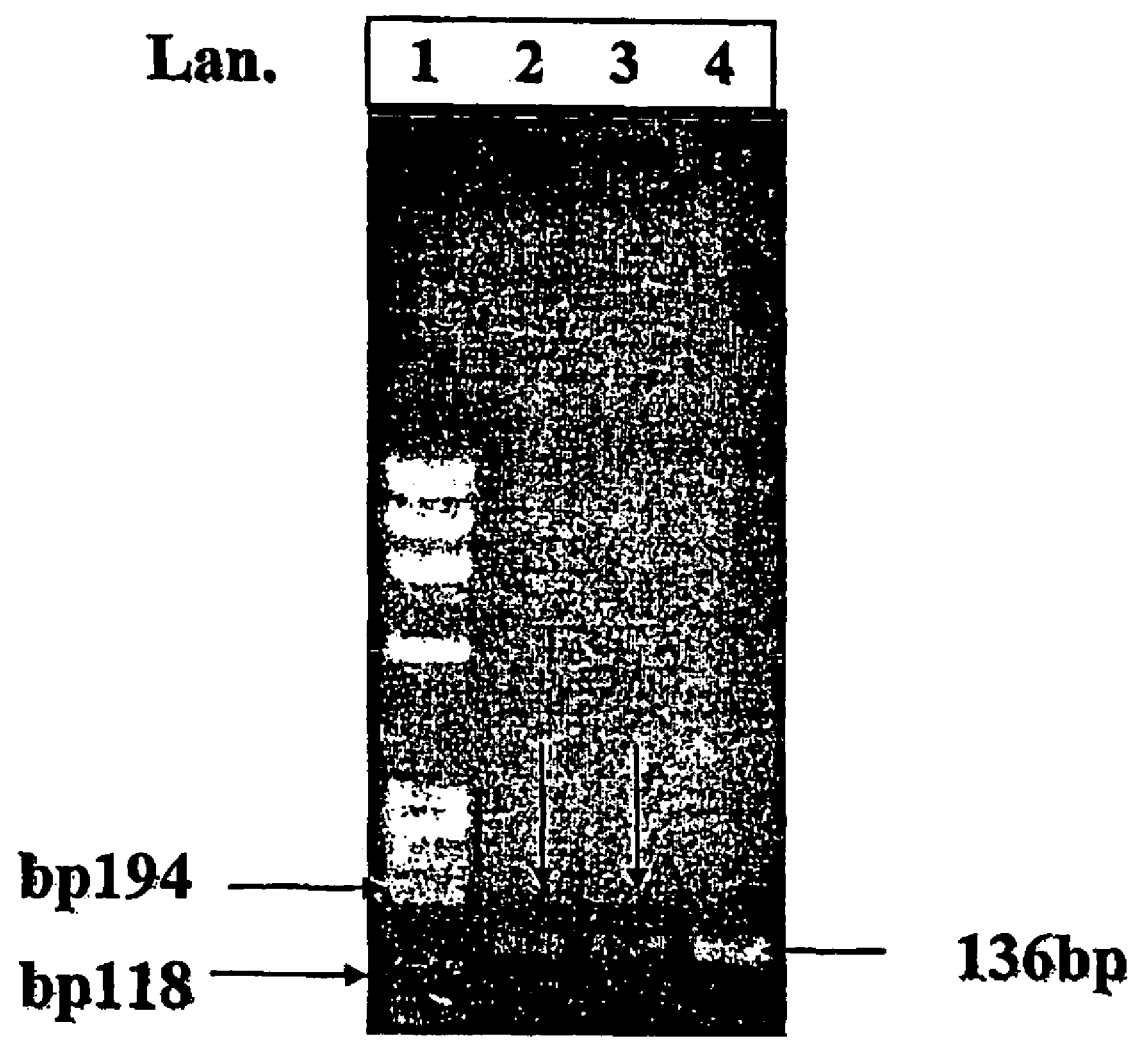

Abbreviations: Al., alone; Mo., month(s).

FIGS. 2A-C: Longitudinal sections of ablated marrow cavities of locally irradiated rat femur bones 15 days post implantation (H&E).
FIG. 2A: Transplantation with DBM, only.
FIG. 2B: Transplantation with DBM+BMC.
FIG. 2C: Transplantation with DBM+BMC+BMP.

Abbreviations: BMC, bone marrow cells; BMP, bone morphogenetic protein; DBM, demineralized bone matrix; HT, hematopoietic tissue. Abbreviations: HT, hematopoietic tissue; H&E, Hematoxylin and Eosin.

FIGS. 3A-F: Correction of the damaged osteo-hematopoietic complex in the ablated marrow cavity by transplantation of demineralized bone matrix and bone marrow cells (Longitudinal section of an ablated marrow cavity of rat femur bone, Picroindigocarmin staining, Macro—8×/Micro—100×)
FIG. 3A: Immediately after ablation.
FIG. 3B: 30 days post-transplantation of DBM together with BMC.
FIG. 3C: 30 days post-transplantation of DBM and BMC mixture supplemented with BMP.
FIG. 3D: 60 days post-transplantation of DBM together with BMC.
FIG. 3E: 150 days post-transplantation of DBM together with BMC.
FIG. 3F: Control, non-ablated femur bone.

Abbreviations: D., day(s); Po. Abl., post-ablation; Po. Transpl.; post-transplantation; N. Abl. Fe. Bo.; non-ablated femur bone.

FIGS. 4A-E: Laser Capture Microdissection (LCM) and PCR analysis of cells captured from the newly reconstituted hematopoietic complex of the ablated marrow cavity (1 month after transplantation of DBM+BMC).
FIG. 4A: Left, rat ablated femur. Right, micrograph of target area for LCM in the ablated marrow cavity of the femur.
FIG. 4B: Laser shot area of reconstituted bone marrow.
FIG. 4C: Laser shot caps (cells captured for the PCR analysis).
FIG. 4D: Higher magnification (×10) of laser shot caps.
FIG. 4E: PCR analysis of donor derived cells harvested by LCM. Lanes: 1, DNA size markers ($\phi$×714 cut with HaeIII), top and bottom arrows on the left point to the 194 bp-long and 118 bp-long bands, respectively; 2, male rat DNA derived from trabecular bone area of female rat ablated marrow cavity; 3, male rat DNA derived from marrow area of female rat ablated marrow cavity; 4, internal positive control, DNA from male blood. The PCR results confirm the presence of donor derived cells in the newly reconstituted hematopoietic complex.

Abbreviations: D., day(s); Po. Abl. Mar. Cav., post-ablated marrow cavity; Targ. Ar. LCM AMC, target area for laser capture microdissection of ablated marrow cavity; Mar., marrow; Lan., lanes; Det. Don. Der. Cel. PCR Anal., detection of donor-derived cells by PCR analysis.

FIGS. 5A-J: Photomicrographs of mice kidney sections after transplantation under the kidney capsule (Picroindigo-carmin, PIC staining).

FIG. 5A: 1 month post-transplantation with DBM alone.
FIG. 5B: 1 month post-transplantation with BMC+DBM.
FIG. 5C: 1 month post-transplantation with BMC+DBM together with BMP.
FIG. 5D: 4 months post-transplantation with DBM alone.
FIG. 5E: 4 months post-transplantation with BMC+DBM.
FIG. 5F: 4 months post-transplantation with BMC+DBM together with BMP.
FIG. 5G: 12 months post-transplantation with DBM alone.
FIG: 5H: 12 months post-transplantation with BMC+DBM.
FIG. 5I: 12 months post-transplantation with BMC+DBM together with BMP.
FIG. 5J: 4 months post-transplantation with BMC only Abbreviations: Al., alone; Mo., month(s)

DETAILED DESCRIPTION OF THE INVENTION

The following abbreviations are utilized throughout this specification:
BM: bone marrow
BMC: bone marrow cell(s)
BMP: bone morphogenetic protein
BMT: bone marrow transplantation
CFU-S: spleen colony forming unit
DBM: demineralized bone matrix
GVHD: graft versus host disease
HVGD: host versus graft disease
LCM: Laser Capture Microdissection
MBM: mineralized bone matrix
MDS: myelodysplastic syndrome
RAEB: refractory anemia with excess blasts (one type of MDS)
RAEB-T: refractory anemia with blastic transformation In search of improving bone marrow transplantation procedures, the inventors have found that using a composition comprising BMC and DBM and/or MBM results in simultaneous development of hematopoietic and stromal tissues (including the hematopoietic microenvironment), originating from the same donor. Moreover, an additional advantage of the BMC-DBM mixture in allogeneic bone marrow transplantation is in facilitating allogeneic hematopoietic stem cell engraftment and reconstitution of hematopoiesis, which is supported by the simultaneous development of the stromal microenvironment originated from the stromal precursor cells from the same donor.

As a result of the inventors' efforts, they have arrived at the present invention which relates to compositions comprising a mixture of bone marrow cells (BMC) and demineralized and/or mineralized bone matrix (DBM and MBM, respectively) and to their novel uses in bone marrow transplantation.

Thus, in a first aspect, the present invention relates to a composition comprising bone marrow cells (BMC) and demineralized bone matrix (DBM) and/or mineralized bone matrix (MBM), optionally further comprising pharmaceutically acceptable carrier and/or diluent.

DBM and MBM may be used in combination or separately in the composition of the invention. In the experiments using BMC in combination with MBM rather than DBM (FIG. 1), the inventors observed that that the main difference between the two bone matrices was a delayed bone formation with MBM. Transplantation of a mixture of the two (DBM and MBM) together with BMC should enable the combination of the advantages of both, i.e. significantly prolonging the period of osteogenic activity (with DBM acting fast and MBM after a delay). Also, since MBM particles are much more dense and hard when compared to DBM particles, the admixture of MBM could be useful when shape preservation of the implant throughout the period of new tissue formation is needed. The ratios of BMC:MBM, and BMC:DBM:MBM will thus depend on the specific needs.

In a further embodiment, the DBM and/or MBM from the composition of the invention are in powder or slice form. The DBM used in the composition of the invention may be of particle size of about 50 to 2500μ. Preferably, the particle size of the DBM is about 250 to 500μ.

Nevertheless, DBM is a preferred ingredient in the composition of the invention, in view of its advantageous ability to combine all the features needed for making it an excellent carrier for mesenchymal progenitor cells.

1. DBM exhibits properties of conductive scaffolding essential for the engraftment of mesenchymal progenitor cells, their proliferation and differentiation.
2. Further, DBM is the natural source of BMPs (bone morphogenetic proteins) active in stimulating the development of hematopoietic environment, thus fulfilling also the inductive function.
3. DBM has very low immunogenicity when used as a xenograft, and non-immunogenic at all when used in allogeneic combinations.
4. DBM can be provided as an amorphous powder that can be injected locally, without major surgical intervention, preferably intra-osseous.

The ratio between BMC and DBM comprised in the composition of the invention may be of 10 parts of BMC concentrate to 0.5 part of DBM (volume/volume), preferably 56 parts of BMC concentrate to 1 part of DBM (volume/volume). The inventors have established that most preferably, said ratio is 4 parts of BMC concentrate to 1 part of DBM (volume/volume).

In a second aspect, said composition comprising BMC and DBM and/or MBM is for use for bone marrow transplantation into a mammal, wherein said mammal is preferably a human.

The transplantation site of the composition of the invention may be an extra-skeletal site, wherein said extra-skeletal site is selected from the group consisting of the kidney capsule, muscles and abdominal wall. As shown in Example 1A, the subcapsular space of the kidney supplies all the necessary local conditions supporting the formation of osteo-hematopoietic complex developing from the implanted cells. Thus the subcapsular space of the kidney could serve as a kind of "in vitro tube" allowing following up the activity of implanted cells. The suspension of bone marrow cells contains mesenchymal progenitor cells capable of building fully developed hematopoietic microenvironment, when transplanted under the kidney capsule with the inductive and conductive support of DBM. Thus, new hematopoietic microenvironment developed from the mesenchymal progenitor cells present in the bone marrow cell suspension, due to the inductive and conductive influences of DBM, and it is capable of long-term maintenance, remodeling and self-renewal, as well as supporting normal three-lineage hematopoiesis for at least one year, which in case was compatible with the life-span of the experimental mammal.

Alternatively, said transplantation site may be a bone marrow cavity. As shown in Example 1B, extensive development of active hematopoiesis is seen when DBM, together with BMC, is transplanted into ablated bone marrow cavity (FIGS. 3B and 3D). It is for the first time that the entire osteo-hematopoietic complex consisting of trabecular bone, hematopoietic microenvironment (of stromal origin) and hematopoietic tissue has been successfully transferred directly into ablated bone marrow cavity in a one-step transplantation procedure. This experiment proved possible the intrafemural transplantation of bone marrow cell suspension containing both hematopoietic and mesenchymal progenitor cells, together with DBM, which possesses inducing and conducive properties for development of hematopoietic microenvironment. This hematopoietic microenvironment plays essential supportive and regulating roles for the development and functioning of the hematopoietic tissue. The newly formed, donor-derived osteo-hematopoietic complex is capable of long-term maintenance, remodeling and self-renewal, as well as active hematopoietic production.

In another embodiment, the composition of the invention further comprises a bone morphogenetic protein (BMP).

As the inventors show, several hamatopoietic areas are seen after transplantation with BMC together with DBM (see, for example, FIG. 2B). However, these areas are even more prominent when BMP is added to the transplantation mixture (see, for example, FIG. 2C). Therefore, the addition of BMP enhances the activity of the composition of the invention, by accelerating the development of the stromal microenvironment supporting hematopoiesis.

The composition of the invention, comprising BMC and DBM and/or MBM, has the major advantage of transplantation of donor multifunctional populations of cells, directly into the marrow cavity of the recipient or extraskeletally, which provides for full development often self-maintained osteo-hematopoietic complex of the donor origin, within the bone or in an extraskeletal site of the recipient. In human adults, red (hematopoietic) bone marrow in long bones tends to be replaced by yellow (fatty) bone marrow. The new approach of the present invention will further facilitate replacing fatty, fibrotic or otherwise malfunctioning bone marrow stroma in human bones. It is further expected that combined stromal and hematopoietic stem cells transplantation, using a one-step procedure, would expand the applicability of bone marrow transplantation (BMT in clinical practice, particularly in improving or enhancing of hematopoiesis, inducing transplantation tolerance, etc.

In yet another embodiment, the DBM and/or MBM comprised within the composition of the invention is of vertebrate origin, and it may be of human origin.

In a further embodiment, the DBM and/or MBM from the composition of the invention are in powder or slice form.

In a yet further embodiment, the composition of the invention is for transplantation into a bone marrow cavity, for restoring and/or enhancing the formation of hematopoietic microenvironment originating from the transplanted BMC. In addition, the composition of the invention is for transplantation into an extra-skeletal site for the development of hematopoietic microenvironment originating from the transplanted BMC.

The composition of the invention shall improve the engraftment of hematopoietic precursor cells transferred within transplanted BMC, for treatment of disorders associated with the malformation, malignancy and/or dysfunction of the bone marrow.

Thus, in an even further embodiment, the composition of the invention is for use in the treatment of a patient suffering from a hematopoietic and/or bone disorder, wherein said hematopoietic disorder is selected from a deficiency of, an abnormality or malignant stem cells and/or their products, a genetic disorder which results in abnormal stem cells and/or their products, abnormal bone structure, integrity or composition and hematopoietic disorders of malignant origin.

As previously mentioned, the composition of the invention may optionally further comprise pharmaceutically acceptable carrier and/or diluent.

A pharmaceutically acceptable (or physiologically acceptable) additive, carrier and/or diluent mean any additive, carrier or diluent that is non-therapeutic and non-toxic to recipients at the dosages and concentrations employed, and that does not affect the pharmacological or physiological activity of the active agent.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially pages 1521-1712 therein.

The composition of the invention may optionally even further comprise additional active agents. Active agents of particular interest are those agents that promote tissue differentiation or infiltration, such as growth factors. One example is BMPs, which may enhance the activity of the composition of the invention. Other exemplary growth factors for this purpose include, epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and growth hormone. Other active agents may be anti-rejection or tolerance inducing agents, as for example immunosupressive or immunomodulatory drugs, which can be important for the success of bone marrow transplantion.

The intra-osseous BMC transplantation procedure using the composition of the present invention has some major advantages, inter alia:

1. Avoiding considerable non-specific loss of hematopoietic stem cells anchored in non-hematopoietic organs when injected intravenously.
2. Improving compatibility and contact between newly formed stromal microenvironment and hematopoietic cells originating from the same donor.
3. Replacing fatty, fibrotic or otherwise abnormal bone medullar spaces with active trabecular system supporting active multilineage hematopoiesis.
4. Feasibility in inducing mixed hematopoiesis with less graft v. host disease (GVHD) and host v. graft disease (HVGD) due to the better compatibility of immunocompetent cells of donor and recipient generated together on the stroma of donor and recipient-type.

In another aspect, the invention relates to a method for transplantation/implantation into a mammal of BMC, containing mesenchymal stem cells, in admixture with DBM and/or MBM, which will support and stimulate the development of mesenchymal stem cells. Said method comprises introducing into said mammal a mixture of BMC with DBM and/or MBM, said mixture optionally further comprising pharmaceutically acceptable carrier and/or diluent.

The method of transplantation of the invention shall induce a stromal microenvironment that supports hematopoiesis, which originates from the transplanted BMC, more specifically from mesenchymal stem cells present in BMC.

In one embodiment, the mixture of the invention is optionally encapsulated within normal tissue membrane and/or within a selective biocompatible membrane that allows penetration of nutrients, cytokines and cells and retains the DBM and/or MBM particles within said membrane(s). Said membrane(s) is useful for providing or enriching the biologic products secreted by the hematopoietic cells or stromal microenvironment in the treatment of deficiency disorders, enhancing donor cell engraftment and for induction of mixed chimerism, which is important for induction of transplantation tolerance.

In another embodiment, said mixture is introduced into a bone marrow cavity of said mammal and/or into an extra-skeletal site of said mammal. The extra-skeletal site of transplantation is selected from the group consisting of the patient's kidney capsule, muscles, abdominal wall, as well as kidney, liver or heart capsule of the allograft for tolerance induction.

In yet another embodiment, the mixture used in the transplantation method of the invention further comprises a BMP.

In a further aspect, the invention relates to a method of treating a hematopoietic disorder and/or a disorder associated with malformation, malignancy and/or dysfunction of the bone marrow and wherein bone marrow transplantation is required, for a mammal in need of such treatment. Said method of the invention comprises administering into a bone marrow cavity or extra-skeletal site of said mammal a mixture of BMC with DBM and/or MBM, wherein said mixture optionally further comprises a pharmaceutically acceptable carrier and/or diluent.

In one embodiment, said mixture used in said method of the invention optionally further comprises a BMP.

The procedure of applying the composition of the invention into either an extraskeletal site or into a BM cavity, comprises the following steps:

1. Selecting the source for BMC. The donor may be of allogeneic type or the BMC may be obtained from the same treated subject (autologous transplantation). The BMC is aspirated from the donor by standard procedure. From the total amount aspirated, one portion will be the BMC comprised in the composition of the invention, and another portion may be optionally injected intravenously (i.v.) into the patient in need of the treatment. These two parts of the aspirated BMC may be divided at any proportion. Preferably, 2 parts of the aspirated BMC is injected i.v., while 1 part undergoes centrifugation, its volume is reduced, resulting in the BMC concentrate, which then is mixed with the DBM in the ratio specified below.

2. Selecting the source of DBM and/or MBM. The DBM is supplied commercially and since it is not immunogenic, there are no limitations for a specific donor. DBM and/or MBM may be in a powder, granules or in slice form. The DBM used in the composition of the invention may be of particle size of about 50 to 2500μ. Preferably, the particle size of the DBM is about 250 to 500μ.

3. Preparing a composition comprising a suspension of BMC, DBM and/or MBM. The ratio between BMC and DBM comprised in the composition of the invention may be of 10 parts of BMC concentrate to 0.5 part of DBM (volume/volume), preferably 5 parts of BMC concentrate to 1 part of DBM (volume/volume). The inventors have established that most preferably, said ratio is 4 parts of BMC concentrate to 1 part of DBM (volume/volume). Optionally the composition may contain BMP. The composition can be administered either by a surgical procedure, or by non-invasive injection. Alternatively, the composition may be administered so that it is encapsulated within normal tissue membranes. Still alternatively, the composition may be contained within a membranous device, made of a selective biocompatible membrane that allows cells, nutrients, cytokines and the like to penetrate the device, and at the same time retains the DBM and/or MBM particles within the device. Such a membranous device is preferably surgically introduced.

4. Providing a biologic glue or scaffold, preferably consisting of fibrinogen and thrombin, which is used for fixation and/or reshaping of the implant composition at the site of implantation.

In another embodiment, said method of the invention further comprises administering to said patient a bone marrow stem cell suspension, preferably by combined intravenous and intraosseous infusion, or alternatively administering intravenous into one of the compartments, i.e. a membranous device, or a scaffold, an extraskeletal site such as the subcapsular space of the kidney, for production of extraskeletal hematopoietic territory.

In yet another embodiment, the BMC used in said method of the invention are allogeneic or said mammal's own.

In yet a further embodiment, the DBM or MBM used in said method of the invention comprises a demineralized and/or mineralized bone slice, respectively.

It is an additional object of the present invention to facilitate the BMT also in those cases in which BMP is used for non-hematological purposes, such as induction of transplantation tolerance for organ transplantation and as a platform for adoptive allogeneic cell-mediated immunotherapy by infusions of naive or immune donor lymphocytes into the recipient.

The invention is also aimed at the induction of host-versus-graft transplantation tolerance to donor alloantigens, in the setting of perfused or cellular allografts or xenografts, when said donor-derived bone marrow combined with DBM or MBM is administered into an allograft, xenograft, or heterotopic organelles, created for induction of tolerance by establishing a state of mixed chimerism.

A last aspect of the invention relates to a kit for transplantation into a mammal of BMC in admixture with DBM and/or MBM, wherein said kit comprises:

(a) DBM and/or MBM in a compacted form;

(b) a BM aspiration needle;

(c) an intra-osseous bone drilling burr;

(d) a needle with a thick lumen for infusion of viscous BMC-DBM or BMC-DBM mixture;

(e) a two-way lumen connector for simultaneous mixing of BMC-DBM together with diluent for dilution of the composition of the invention;

(f) a medium for maintaining BMC; and optionally (g) cryogenic means for handling and maintaining BMC or BMC together with DBM or MBM.

The kit of the invention may optionally comprise needles for intra-venous injection.

The major advantage of the present invention, comprising administering a mixture of bone marrow cells and demineralized or mineralized bone matrix intra-osseously, lies in the feasibility to generate new microenvironment and hematopietic system derived from progenitor cells provided with the graft. Unlike treatment of patients with hematologic malignancies caused by malignant stem cells or their progeny, where replacement of the marrow stem cells in parallel with irradiation of all malignant cells may be curative, in patients with problems involving both abnormal stem cells and bone marrow microenvironment, stem cell transplantation alone may not be sufficient for correction of the basic disease. In other words, whereas in some hematologic malignancies replacement of the 'seeds' may suffice, replacement of 'seed and soil' may be required and mandatory in patients with associated abnormal milieu that may not provide the newly grafted stem cells the proper signals for normal maturation and differentiation. This appears to be the cause of failure following BMT for such patients, where engraftment problems may be observed with no signs of rejection. It can be foreseen, therefore, that in patients with normal cytogenetic analysis and no evidence of malignant stem cell disease, the composition of the invention comprising autologous BMC with DBM may suffice for correction of hematopoiesis. In contrast, in patients with pre-malignant or overtly malignant stem cells, the BMC comprised in the composition of the invention will have to be from an allogeneic donor, for optimal facilitation of de novo hematopoietic reconstitution. The beneficial effects of autologous BMT in a small proportion of patients with MDS, together with the results shown in Example 2, suggest that such a strategy is indeed valid and may be feasible. In conclusion, suitable candidates for the suggested treatment may be patients with MDS with grossly abnormal stroma, as well as patients suffering from hematologic malignancies with secondary or primary myelofibrosis, as well as patients with other primary or secondary involvement of marrow microenvironment due to any primary or secondary bone disease, or due to chemotherapy or radiation can be suitable.

Many publications are cited throughout this application. The contents of these references are fully incorporated herein by reference.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials and Methods

1. Animals 8-week old C57BL/6 male mice and Lewis male rats with body weight of 180-200 g were used as bone donors, for both matrix preparation and BMC. Mice and rats from the same batches were used as the recipients.

2. Preparation of Demineralized Bone Matrix (DBM) and Mineralized Bone Matrix (MBM)

Demineralized bone matrix (DBM) was prepared as described [Reddi and Huggins (1973) id ibid.], modified by the inventors. Rats diaphyseal cortical bone cylinders were cleaned from bone marrow and surrounding soft tissues, crumbled and placed in a jar with magnetic stirring. Bone chips were rinsed in distilled water for 2-3 hrs; placed in absolute ethanol for 1 hr and in diethyl ether for 0.5 hr, then dried in a laminar flow, pulverized in a mortar with liquid nitrogen and sieved to select particles between 400 and 1,000 µ. The obtained powder was demineralized in 0.6M HCl overnight, washed for several times to remove the acid, dehydrated in absolute ethanol and diethyl ether and dried.

Mineralized bone matrix (MBM) was prepared according to the same procedure, without the demineralization with HCl step.

Experiments with mice were performed using demineralized tooth matrix prepared from incisors dissected out from adult mice, as previously described [Gurevitch et al. (1999) id ibid.]. In case of rats and larger animals the cortex of long bones is the appropriate material for preparation of DBM. In mice, however, only DBM prepared from dentine is active enough and produces reproducible results.

All steps, except the drying step, were performed at 4° C. to prevent degradation of bone morphogenetic proteins (BMP) by endogenous proteolytic enzymes. The matrices were stored at −20° C.

3. Preparation of the Implanted Material

Preparation of Donor BMC Suspensions for Transplantation

The femurs of donor mice or rats were freed of muscle. Marrow plugs were mechanically pressed out of the femural canal by a mandrin. Concentrated single cell suspensions of BMC were prepared by disrupting 4-5 femural plugs in 100 µl of RPMI 1640 medium (Biological Industries, Beit Haemek, Israel). The number of nucleated cells per femural bone marrow plug is usually rather stable (about $10^7$ cell/plug for a C57BL/6 male, 8-week old mouse). Several reproducible verifications showed that a single cell suspension of BMC prepared for transplantation contains approximately $3\times10^8$ cells/ml.

Composition of the Grafts

The following components could be present in the grafts (each graft had its own combination, as specified in the Figures and in the Examples):

1. 20 µl of BMC suspension ($3\times10^8$ cells/ml);
2. 4 mg of DBM (or MBM) were used in experiments with rats; 2 mg in experiments with mice;
3. 0.5 µg BMP-2 (R & D systems, USA) was added to the mixture in some of the experiments The exogenous BMP that was optionally added to the composition of the invention is not a mandatory ingredient. DBM exhibits properties conducive for the engraftment of mesenchymal progenitor cells transplanted within BMC suspension, for their proliferation and for differentiation in the course of bone and cartilage formation. At the same time, DBM is the natural source of BMPs, active in stimulating osteo- and chondrogenesis, thus fulfilling also the inducing function. Addition of exogenous BMPs may enhance the efficiency of the induction.

4. Transulantation at a Site Under the Kidney Capsule

Anaesthetized rats or mice were used as recipients. A small cut was made in the renal capsule and the transplanted material was inserted using a concave spatula.

5. Local Ablation of Recipient's Bone Marrow in the Medullar Cavity of the Bone

Rats were anaesthetized, and right leg was irradiated with 1,000 cGy. Radiation was delivered by a Phillips X-ray unit (250 kV, 20 mA) at a rate of 70 cGy/min, using a Cu 0.2-mm filter. The source-to-skin distance was 40 cm.

After local irradiation, a small incision was made over the knee joint of the right leg. The medullar cavity of the femur was entered with a bone marrow aspiration needle and the bone marrow was evacuated. The remainders of the bone marrow were washed out with 3 ml of phosphate buffered saline (PBS) using a syringe with a 19-gauge needle.

6. Implantation of a Mixture of BMC and Demineralized Bone Matrix into Ablated Medullary Cavity of the Bone Following anesthesia, the knee joint was accessed by a medial parapatellar incision, the patella temporarily displaced sidewards, local ablation of BM was performed as described and the desired material implanted into the bone cavity. Cells and bone matrix were placed in a small micropipette tip, which was inserted into the hole in the bone, and the transplantation material was pushed inside the bone cavity with a mandrin. The site of the incision was covered with fibrinogen-thrombin tissue adhesive glue, the patella was returned into its place and the incision was sutured with bioresorbable thread. Skin was closed with stainless clips.

7. Laser Capture Microdissection (LCM) and Polymerase Chain Reaction (PCR) Analysis of the Reconstituted Osteo-hematopoietic Complex After Implantation of BMC and Demineralized Bone Matrix into Ablated Marrow Cavity In the experiments in which BMC of male donors mixed with DBM was transplanted into the ablated marrow cavity of femural bone of female recipients, the donor origin of newly formed trabecular bones, as well as the donor origin of reconstituted hematopoietic tissue were identified by PCR analysis [An, J. et al. (1997) *J Androl.* 18(3):289-93]. The new technology of Laser Capture Microdisoection (LCM) allowing isolation of individual cells from tissue sections under precise microscopic control was used to harvest separately cells from newly formed bone and hematopoietic tissue. PCR analysis of harvested cells (about 200-300 cells per test) was performed using the set of primers specific to the Sry gene—the sex determination region of Y chromosome.

8. Histolosical Evaluation

The autopsied material was fixed in 4% neutral buffered formaldehyde, decalcified, passed through a series of ethanol grades and xylene, and then embedded in paraffin. Serial sections of 5-7 microns were made and one set of representative serial section was stained with Hematoxylin and Eosin, and the other with Picroindigocarmin.

Example 1

Transplantation of BMC Together with Demineralized (or Mineralized) Bone Matrix into the Bone Marrow Cavity or into the Sub-capsular Space of the Kidney in Rats In the following examples, the experimentation involved in the development of the composition of the invention, it is shown that the mesenchymal stem cells persisting in the bone marrow BM) can be induced to form bone and supportive hematopoietic microenvironment when transplanted together with DBM into bone marrow cavity or extraskeletally, into the sub-capsular space of the kidney. In two sets of experiments, one carried out in rats and the other in rats and mice, DBM or MBM were implanted alone or together with BMC supplemented or not supplemented with additional bone morphogenetic protein-2 (BMP-2) (at least 12 transplants per group).

A one-step transplantation procedure was established in which a composition of BMC and demineralized (or mineralized) bone matrix powder (DBM or MBM) was inserted into the bone marrow cavity or extra-skeletally (into the sub-capsular space of the kidney) in order to induce (a) the formation of a trabecular bone, (b) supportive hematopoietic microenvironment and (c) hematopoiesis originating from mesenchymal and hematopoietic precursor cells present in transplanted bone marrow.

A. Transplantation into the Sub-capsular Space of the Kidney

The space under the kidney: capsule was selected as the site of transplantation, since it has been previously shown that it has no cells which could be induced into osteogenesis and to build a bone, at least within the period of 2-3 months [Gurevitch, O. A. et al. (1989) *Hematol Transfusiol* 34:43-45 (in Russian)].

It was observed that in rats, one month after transplantation of DBM (or MBM) without BMC, there were no signs of hematopoiesis. Implanted matrix particles were still present and non-degraded at the site of transplantation (FIGS. 1A and 1C). In contrast, in sites where DBM was transplanted together with BMC, active multi-lineage hematopoiesis was observed, and profound degradation of transplanted matrix particles could also be seen (FIG. 1B). Formation of new bone capable of supporting hematopoiesis was also observed when MBM together with BMC was implanted under the kidney capsule (FIG. 1D). However, degradation of transplanted MBM particles, as well as the development of trabecular system, were slightly delayed comparatively with the cases in which BM cells were transplanted together with DBM.

Interestingly, addition of exogenous BMP to the BMC+DBM graft accelerated the development of stromal microenvironment supporting hematopoiesis. Transplantation of BMC alone did not result in development of hematopoietic tissue (FIG. 1J).

Six months after transplantation of DBM (or MBM) without BMC, there were still no signs of hematopoiesis. Implanted matrix particles were still present at the site of transplantation (FIGS. 1E and G). In contrast, six months after transplantation of DBM together with BMC, newly formed hematopoietic sites continued self-maintaining and remodeling. Wide cavities of active hematopoiesis characteristic for well developed hematopoistic areas were observed (FIG. 1F). Six months after transplantation of MBM together with BMC, newly formed hematopoietic sites are almost morphologically undistinguishable from those developed on transplantation of DBM together with BMC (FIG. 1H). After one year, the new hematopoietic sites developed as a result of transplantation of DBM (or MBM) together with BMC continued self maintaining without any signs of degeneration. (FIG. 1I)

A similar set of experiments carried out in mice gave similar results, i.e. combined transplantation of DBM and BMC induced development of a new, functionally active hematopoietic site capable of life-long self maintenance under the kidney capsule (FIGS. 5B, 5E and 5H), while transplantation of DBM or BMC alone did not display the same result, i.e., no formation of new hematopoietic tissue was observed (FIGS. 5A, 5D and 5G). Addition of BMP-2 enhanced the development of new hematopoietic site (FIGS. 5C, 5F and 5I).

B. Transplantation into the Bone Marrow Cavity

In another set of experiments, carried out in rats, DBM, together with BMC or with BMC and BMP, was implanted directly into the ablated femoral marrow cavity of the locally irradiated leg (at least 6 animals in each experimental group). Two weeks after the intrafemural implantation of DBM without BMC, new hematopoietic tissue was scarcely seen (FIG. 2A). In contrast, when DBM was implanted together with BMC, newly formed and active hematopoietic tissue was observed (FIG. 2B). Addition of BMP to the graft consisting of DBM and BMC enhanced the development of the hematopoietic complex (FIG. 2C).

One month after direct transplantation of DBM together with BMC into ablated bone marrow cavity extensive development of active hematopoiesis was seen, and partially degraded DBM particles were still present in the diaphyseal area of the femoral cavity (FIG. 3B). When BMP was supplemented to the transplanted mixture, the process of osteohematopoietic complex development was accelerated, only small particles of DBM are still seen in the femural shaft (FIG. 3C). Two months after intra-femur transplantation of the DBM-BMC mixture, the osteohematopoietic complex of the femural shaft of the treated bone is almost undistinguishable from an undamaged one (FIGS. 3D and 3F, respectively). Five months after transplantation the new osteohematopoietic complex continued to self-maintaining without any signs of degeneration (FIG. 3E). Well developed and actively functioning osteo-hematopoietic complex of the femural shalt continued self-maintaining and remodeling throughout the whole life-span of the recipient.

In the experiments in which BMC of male donors mixed with DBM were transplanted into ablated marrow cavity of femural bone of female recipients, the donor origin of newly formed hematopoietic tissue was documented by PCR analysis of individual cells (about 70-100 cells per test), which were isolated from tissue sections under precise microscopic control using LCM techniques (FIG. 4).

Example 2

Treatment of Terminally Ill Patients

As seen in Example 1, under proper conditions, hematopoietic stem cells can create fully functional hematopoietic bone, but only if inoculated together with normal marrow stromal cells. Likewise, bone morphogenetic proteins (BMPs) can enhance bone marrow cellularity, stem cell engraftment and the efficacy of rescue of myeloablated recipients. Histologic examination of newly derived bones from mixtures of DBM and marrow stem cells under the kidney capsule featured fully functional hematopoietic bone generated within 2 to 4 weeks. The feasibility of induction of extra-medullary hematopoiesis suggested that the inventors' new method might be applicable for induction of microenvironment in situations where patient's own microenvironment is damaged or absent. Based on the above-mentioned observations, the inventors hypothesized that new bone formation with microenvironment and active hematopoiesis may be useful for patients with advanced stage MDS (myelodysplastic syndrome), with abnormal stem calls, for correction of the microenvironment as well as for the replacement of abnormal stem cells.

Preliminary Experience in Pre-clinical Animal Models

Results obtained in lethally irradiated mice, treated with increments of stem cells infused alone or together bone marrow microenvironment, showed that in comparison with stem cells given alone, a lower number of stem cells was sufficient to rescue all the recipients when combined with microenvironment (data not shown). These data support the essential role of microenvironment and the added benefit of combining stem cells and microenvironment for optimal BMT.

Case 1

Z. S., a 53 years old female patient was admitted in early September 2001 to the Department of Bone Marrow Transplantation of the Hadassah University Hospital (Jerusalem, Israel) for the treatment of MDS in transformation to leukemia. The patient presented cytogenetic abnormalities and myelofibrosis, that developed following polycythemia vera previously treated with phlebolomy, busulfan, hydroxyurea and interferon. Cytogenetic analysis revealed 46XX+1, der (1;7) (q10;p10) in 4 of 13 mitoses. Allogeneic BMT was the treatment of choice and a matched sibling was indeed located. Patient was conditioned with Fludarabine 30 mg/m$^2$×6; Busulfan 4 mg/Kg×4 and Cyclosporine 3 mg/Kg starting 4 days previous to the transplant. This protocol resulted in prompt engraftment and rapid development of three-lineage hematopoiesis in all patients treated thus far. Unfortunately, although the patient received an adequate number of donor stem cells, 35.7×10$^8$ nucleated cells/Kg, no engraftment was observed until day 22 post-transplantation. Due to complete aplasia, the patient's condition started to deteriorate, requiring administration of antibiotics and to be maintained on platelet transfusions in reverse isolation. A permission to perform the experimental intra-osseous transplantation with the composition of the invention, comprising DBM mixed with donor bone marrow cells, was applied for at the Internal Helsinki Committee of the Hadassah Medical Organization (from the Hadassah University Hospital in Jerusalem, Israel) and at the Ministry of Health of the State of Israel. After obtaining approval from the Internal Helsinki Committee and the Ministry of Health, as well as an informed consent by the patient, intra-osseous transplantation of donor BMC in combination with DBM was done as described below. On Nov. 5, 2001, the patient received a total of 2.93×10$^8$/kg bone marrow derived cells, from the same donor, obtained under epidural anesthesia, this time without any anti-GVHD prophylaxis. Commercial DBM was purchased from Pacific Coast Tissue Bank in Los Angeles, Calif., USA, particle size 250 to 500µ. 2.17×10$^8$/kg bone marrow stem cells were infused intravenously. A total of 20 ml (dry volume) of powder DBM was mixed at a ratio of 1 to 4 volume/volume with a suspension of donor BM concentrate (×5), and injected into four sites (upper portion of the tibia bilaterally and 2 sites of the sacrum). The mixture of DBM and 0.76×10$^8$/kg bone marrow cells was injected with needles used for bone marrow biopsy in routine clinical practice, connected to a 2-way lumen connector for simultaneous mixing of BMC-DBM and diluent, for decreasing the viscosity of the mixture. The procedure was done under sedation and local anesthesia, and was thus totally painless. The day of the procedure was considered day 0. Active and rapid three-lineage hematopoiesis started on day 5, and all blood counts were rapidly back to normal levels. The patient reached an absolute neutrophil count of $1\times10^9$/L on Nov. 9, 2001 and platelet counts >$25\times10^9$/L on Nov. 11, 2001, with platelet counts >$50\times10^9$/L starting from November $15^{th}$. On day 38 after infusion of stem cells and DBM, the patient was discharged in excellent general condition. A 100% engraftment of donor hematopoietic cells was confirmed by the presence of male DNA in the peripheral blood cells, detected by PCR of the Y-chromosome specific, Amelogenine gene. Until the last visit to the clinic, the patient was well, with fully reconstituted three-lineage engraftment and in excellent clinical conditions. A total of 20 mitoses examined after transplantation revealed normal 46XY karyotype.

In summary, this case has been the first case to suggest that correction of hematopoietic microenvironment may support allogeneic stem cells, and that this is feasible by intra-osseous transplantation of donor bone marrow cells mixed with DBM. This case therefore suggests that stem cell transplantation may be enhanced in patients with impaired marrow microenvironment by combining administration of stem cells with DBM.

Case 2

Y. V., a 22 years old male patient, was admitted to the Department of Bone Marrow Transplantation of the Hadassah University Hospital (Jerusalem, Israel) in January 2002 for treatment of pancytopenia, following bone marrow transplantation from a matched sibling due to MDS with excess blasts (RAEB) in 2001. In 1997, at the age of 16 years, T-cell acute lymphoblastic leukemia (T-ALL) was diagnosed and the patient was successfully treated with a standard remission induction and maintenance protocol until 1999. In July 2001, the patient developed secondary MDS, featured by increasing weakness, malaise and progressive pancytopenia. RAEB was confirmed in a bone marrow biopsy. Cytogenetic study indicated deletion of chromosome 5, a chromosomal abnormality typical of MDS. The patient was admitted for bone marrow transplantation, the only possible cure of this condition. In September 2001, the patient underwent allogeneic stem cell transplantation from a fully HLA matched brother, after myeloablative conditioning with fludarabine 30 mg/$^2$ for 6 days and busulfan 4 mg/kg for 4 days. On day 0 he received G-CSF mobilized blood stem cells, in a total of $54\times10^8$ nucleated cells/kg, from his donor. Cyclosporine A (CSA) 3 mg/Kg was given starting 4 days before the transplantation procedure, as the sole anti-GVHD prophylaxis. The post-transplant course was uncomplicated. He engrafted on day 14 and was discharged without major complications. He developed no signs of acute GVHD and was followed in the outpatient clinic.

A month later the patient developed prolonged progressive pancytopenia associated with cytomegalovirus (CMV) antigenemia. After intravenous treatment with ganciclovir, the signs of CMV infection disappeared but the patient continued to be panytopenic. Blood DNA analysis showed that the patient featured mixed donor/recipient chimerism, suggesting co-exiting host hematopoiesis. Bone marrow aspiration revealed MDS, transforming into overt myeloid leukemia, and the patient was readmitted to the Department of Bone Marrow Transplantation. There were no signs or symptoms of GVHD, and therefore CSA was discontinued. The patient was treated with chemotherapy, which consisted of high doses of Ara-C and mitoxantron. On Dec. $23^{rd}$ 2001, the patient received subsequent rescue with very high number ($26\times10^8$ mononuclear cells/kg) of G-CSF mobilized blood stem cells from the same donor, this time without any anti-GVHD prophylaxis. This is the preferable protocol for treatment of post-transplant relapse for induction of maximal graft-versus-leukemia (GVL) effects mediated by donor alloreactive T-cells. Following chemotherapy-induced aplasia (WBC<$0.3\times10^9$/L until day +7), white cell counts ranged between 0.4 and $0.6\times10^9$/L with almost no granulocytes in the peripheral blood smears. Top up infusion with frozen blood stem cells from the same donor ($9,3\times10^8$ mononuclear cells/kg) did not show any increments of neutrophil counts. Treatment with G-CSF (5 and then 10 µg/kg) did not increase the absolute neutrophil count as well. The patient developed persistent low-grade fever for 3 weeks after transplantation, which progressed to 40° C. for 4 days. Despite the severe pancytopenia, the last assay for chimerism by host and donor DNA analysis (VNTR-PCR) on Jan. $13^{th}$, 2002 confirmed 100% donor hematopoiesis, thus confirming lack of rejection as a possible cause of aplasia. Bone marrow aspiration on the same day showed severe hypocellularity with very few precursors, which also confirmed by bone marrow biopsy. In conclusion, the data suggested marrow aplasia despite solid evidence of engraftment of donor hematopoietic cells, most likely due to impaired marrow microenvironment, a life threatening clinical conditions resulting in bone marrow aplasia, with no response to hematopoietic growth factors. It was then decided to re-infuse donor bone marrow cells mixed with DBM into the bone marrow cavity in an attempt to enable rapid engraftment of donor stem cells.

On Jan. 28, 2002, after approval of the Internal Helsinki Committee and of the Ministry of Health, together with an informed consent by the patient, a total of $2.48\times10^8$ mononuclear cells/kg fresh bone marrow cells were aspirated from the same donor under epidural anesthesia. Commercial DBM was purchased from Pacific Coast Tissue Bank (Los Angeles, USA), particle size 250 to 500µ. A total of 20 ml (dry volume) was mixed at 1 to 4 volume/volume with a suspension of donor bone marrow concentrate (×5), and injected into four sites (upper portion of the tibia bilaterally and 2 sites of the sacrum). Two thirds of the cells ($1.65\times10^8$/Kg) were administered intravenously and one third of the cells mixed with DBM containing $0.83\times10^8$ nucleated cells/g were inoculated intraosseously, mostly into the posterior superior iliac spine. The BMC-DBM mixture had to be diluted in order to prevent occlusion of flow into the needle into the marrow cavity. The procedure was done under light anesthesia in the patient's room, using Propofol anesthesia. The mixture of DBM and bone marrow cells was injected with needles used for bone marrow biopsy in routine clinical practice connected to a 2-way lumen connector for simultaneous mixing of DBM and bone marrow cells with buffered saline as diluent, for decreasing the viscosity of the mixture. The procedure was done under sedation and local anesthesia, and was thus totally painless. The day of the procedure was considered day 0. Followinr transplantation, fast reconstitution of hematopoiesis was observed with more than doubling of the white cell count within 4 to 5 days, with levels reaching up $4.9\times10^9$/L on day 8. Platelet counts rose from $10\times10^9$/L to $49\times10^9$/L on day 8, and doubled to $83\times10^9$/L on day 11. In parallel, hemoglobin levels rose spontaneously from 8.0 g % to 10.1 g %. In addition, the patient's condition improved dramatically, his spirits improved and he could be mobilized out of bed. Engraftment was accompanied by signs of graft-vs-host disease with mild rise of bilirubin up to 33 IU, aspartate aminotransferase (AST) rose from 16 to 62 IU, alanine aminotransferase (ALT) from 23 to 90 IU, and lactic dehydrogenase (LDH) rose from 338 to 618 IU. Diarrhea was treated with corticosteroids. Until the last examination, differential count of white blood cells showed up to 84.6% granulocytes, with lymphocytes ranging between 10 to 23%, and monocytes ranging between 10 to 21%. There was no evidence of blasts, and all blood cells were from donor origin as confirmed by VNTR-PCR.

In conclusion, a new transplant procedure involving combined use of intravenous bone marrow-cells and intraosseous transplantation of allogeneic bone marrow cells mixed with DBM, resulted in rapid and full reconstitution of donor hematopoietic cells, in two patients with MDS with previously abnormal bone marrow microenvironment. Our data suggest that a similar procedure may prove useful for treatment of other diseases associated with or caused by abnormal bone marrow microenvironment. This may be either in conjunction with administration of host stem cells following autologous bone marrow transplantation, for patients with normal stem cells, or in conjunction with allogeneic bone marrow transplantation for patients with combined abnormality of bone marrow stem cells and microenvironment, as was exemplified in the two cases presented above.

Furthermore, it seems reasonable to assume that hematopoietic reconstitution by BMC together with DBM may be further enhanced by exogenous enrichment of this mixture with morphogenic growth factors, such as bone morphogenic proteins (BMPs), which are naturally present in DBM.

The invention claimed is:

1. A method of treating a mammal suffering from a hematopoietic disorder wherein bone marrow transplantation is required comprising administering into a bone marrow cavity or extra-skeletal site of the said mammal a mixture of bone marrow cells (BMC) and demineralized bone matrix (DBM) and/or mineralized bone matrix (MBM), said mixture optionally further comprising a pharmaceutically acceptable carrier and/or diluent.

2. The method according to claim 1, wherein said mixture optionally further comprises a bone morphogenic protein (BMP).

3. The method according to claim 1, further comprising administering to said mammal a stem cell suspension.

4. The method according to claim 1, wherein the bone marrow cells (BMC) are allogeneic or said mammal's own.

5. A kit for transplantation into a mammal of bone marrow cells (BMC) in admixture with demineralized bone matrix (DBM) and/or mineralized bone matrix (MBM), wherein said mammal suffers from a hematopoietic disorder wherein bone marrow transplantation is required, said kit comprising:
   a. DBM and/or MBM in a compacted form;
   b. a BM aspiration needle
   c. an intra-osseous bone drilling burr;
   d. a needle with a thick lumen for infusion of viscous bone marrow-DBM or bone-marrow-MBM mixture;
   e. a two-way lumen connector for simultaneous mixing of BMC-DBM or BMC-MBM with the diluent
   f. a medium for maintaining BMC; and optionally
   g. cryogenic means for handling and maintaining BMC or BMC together with DBM.

6. The method according to claim 3, wherein said administration is by intravenous infusion.

7. The method of claim 1 wherein said hematopoietic disorder is selected from a deficiency of stem cells and/or their products, an abnormality of stem cells and/or their products, a genetic or acquired condition which results in abnormal stem cells and/or products and a hematopoietic disorder of malignant origin.

8. The method of claim 1 wherein said hematopoietic disorder affects stromal microenvironment that supports and regulates hematopoiesis.

* * * * *